(12) United States Patent
Muto

(10) Patent No.: US 8,783,867 B2
(45) Date of Patent: Jul. 22, 2014

(54) IMAGE CAPTURE APPARATUS AND METHOD

(75) Inventor: Kenji Muto, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 122 days.

(21) Appl. No.: 13/023,814

(22) Filed: Feb. 9, 2011

(65) Prior Publication Data

US 2011/0199579 A1    Aug. 18, 2011

(30) Foreign Application Priority Data

Feb. 17, 2010    (JP) .................................. 2010-032330

(51) Int. Cl.
*A61B 3/14*    (2006.01)
*A61B 3/10*    (2006.01)
*A61B 3/00*    (2006.01)

(52) U.S. Cl.
CPC .................................. *A61B 3/14* (2013.01)
USPC ............ 351/206; 351/208; 351/221; 351/246

(58) Field of Classification Search
USPC .......................... 351/208, 246, 205, 206, 221
See application file for complete search history.

(56) References Cited

U.S. PATENT DOCUMENTS

| | | | |
|---|---|---|---|
| 7,140,730 | B2 | 11/2006 | Wei et al. |
| 7,549,746 | B2 | 6/2009 | Tsukada et al. |
| 7,980,697 | B2 | 7/2011 | Tsukada et al. |
| 2006/0114411 | A1 | 6/2006 | Wei et al. |
| 2007/0076217 | A1 | 4/2007 | Baker et al. |
| 2007/0222945 | A1 | 9/2007 | Tsukada et al. |
| 2007/0291277 | A1 | 12/2007 | Everett et al. |
| 2009/0190092 | A1 | 7/2009 | Tsukada et al. |
| 2010/0103374 | A1 | 4/2010 | Hirose et al. |
| 2010/0321700 | A1 | 12/2010 | Hirose et al. |

FOREIGN PATENT DOCUMENTS

| | | |
|---|---|---|
| CN | 101072534 A | 11/2007 |
| CN | 101268928 A | 9/2008 |
| JP | 2007-252693 A | 10/2007 |
| WO | 2009/136659 A1 | 11/2009 |
| WO | 2010/101162 A1 | 9/2010 |
| WO | 2010/140476 A1 | 12/2010 |

OTHER PUBLICATIONS

Combined Search and Examination Report under Sections 17 and 18(3) dated Jun. 1, 2011, in counterpart GB Application No. GB1102363.7.
Feb. 22, 2013 Chinese Official Action in Chinese Patent Appln. No. 201110039870.6.

*Primary Examiner* — Jack Dinh
(74) *Attorney, Agent, or Firm* — Fitzpatrick, Cella, Harper & Scinto

(57) ABSTRACT

It has been very cumbersome to determine whether or not alignment is required before the fundus image is acquired after the tomographic image is acquired, causing the reduction in diagnostic efficiency. An ophthalmic apparatus is provided to solve this problem, which comprises an irradiation unit that irradiates an eye to be inspected with a first beam for acquiring a tomographic image of the eye and a second beam for acquiring a fundus image of the eye, the second beam having a beam diameter larger than the beam diameter of the first beam; and a determination unit that, based on information indicating a shift amount between an irradiation position of the first beam in the eye and an ocular axis of the eye, determines whether or not the irradiation position of the second beam falls within a range in which the fundus image can be acquired.

34 Claims, 8 Drawing Sheets

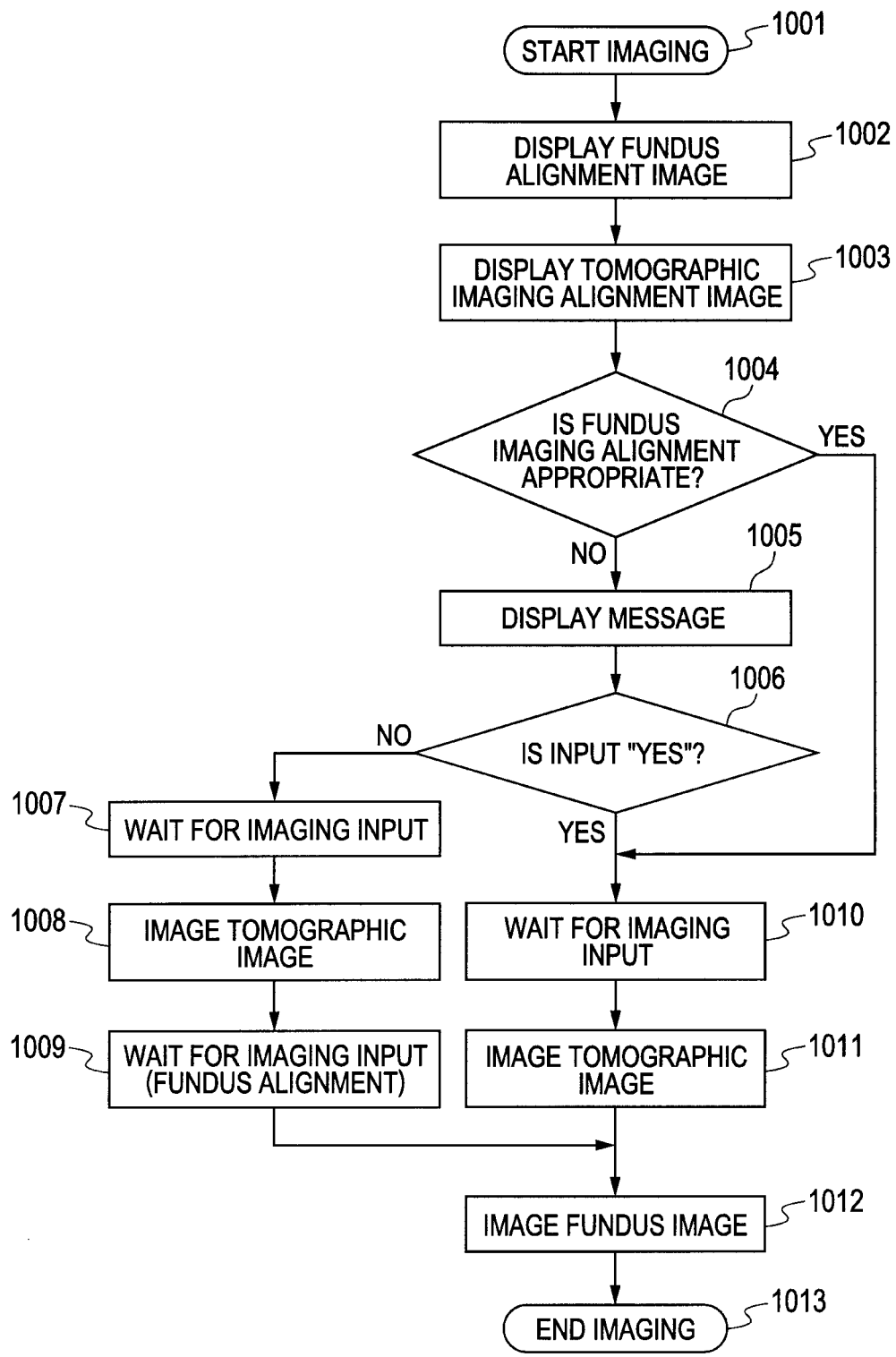

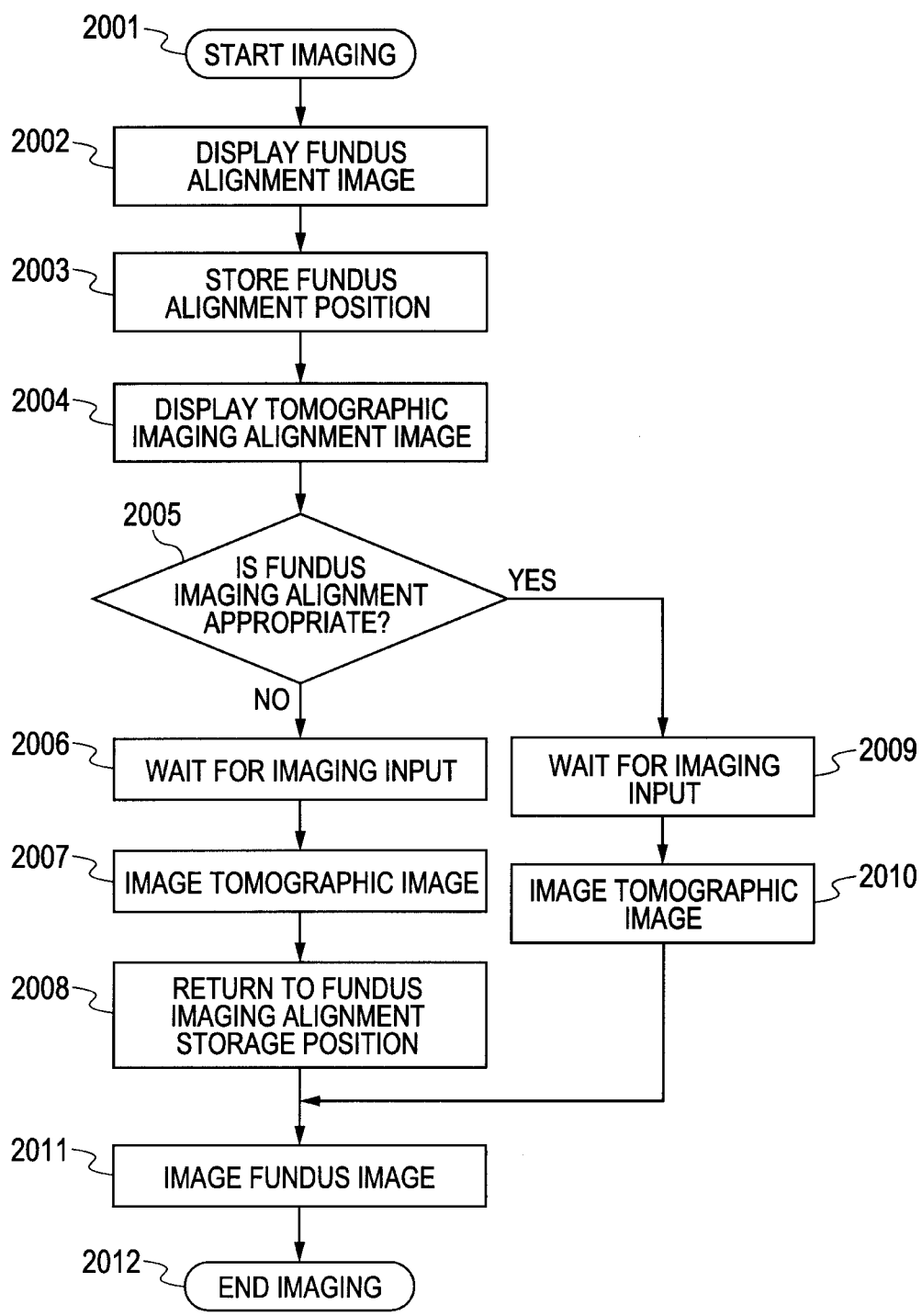

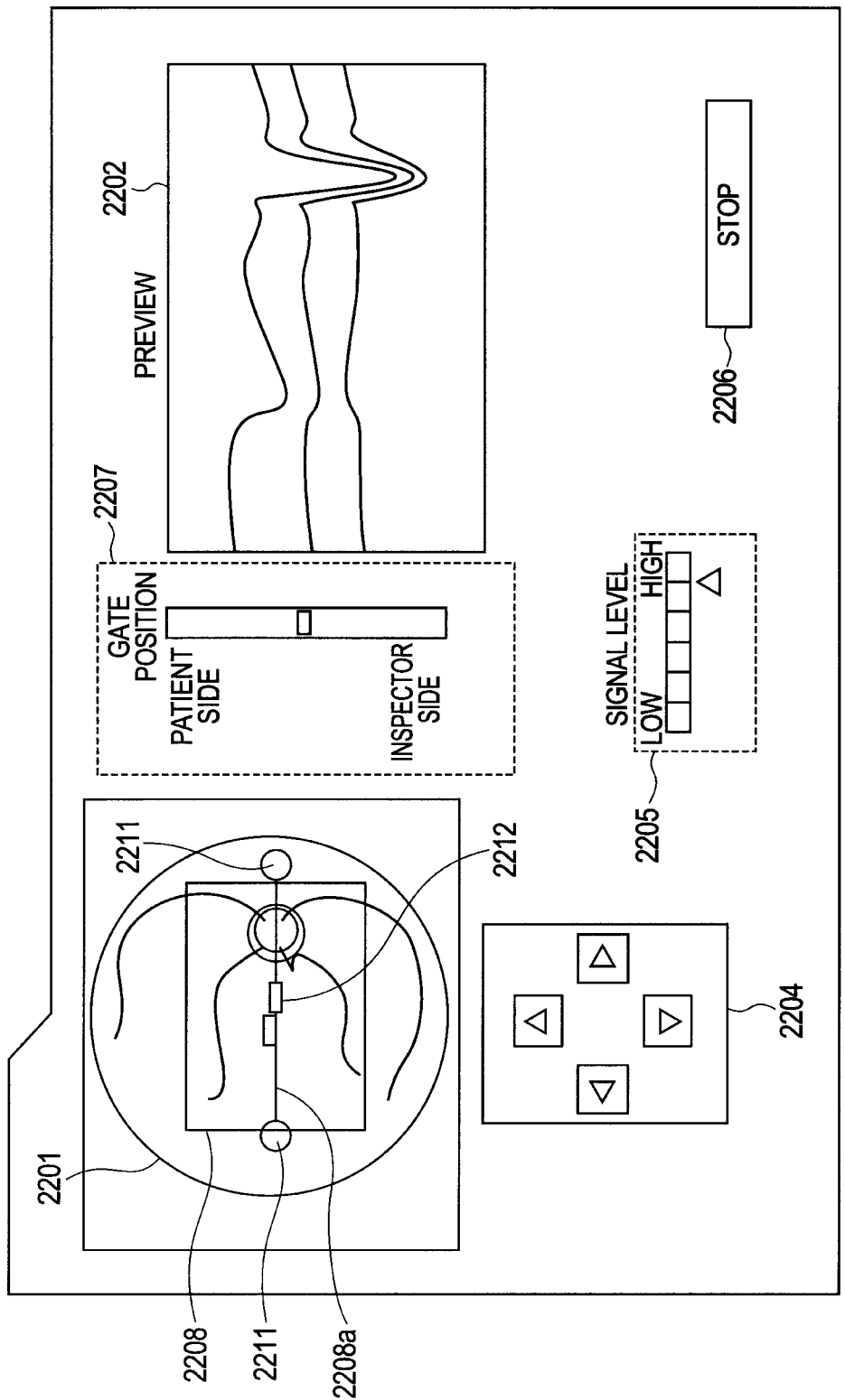

IMAGE CAPTURE APPARATUS AND METHOD

BACKGROUND OF THE INVENTION

1. Field of the Invention

The present invention relates to an image acquisition apparatus which acquires a fundus image and a tomographic image of an eye to be inspected.

2. Description of the Related Art

Japanese Patent Application Laid-Open No. 2007-252693 discloses an apparatus which partially integrates an optical system of optical coherence tomography (OCT) for acquiring a tomographic image of an eye to be inspected with an optical system of a fundus camera (an apparatus for acquiring a two-dimensional (2D) image of a fundus by visible light). In particular, when an operation button of a joystick provided on the fundus camera is pressed, a plurality of 2D tomographic images (known as cross-sectional or B-scan images) is acquired and then a fundus image is acquired by visible light as illustrated in FIG. 6A and the like.

In general, the observation pupil diameters (the diameter of a beam emitted on an anterior ocular segment of an eye to be inspected) of the OCT optical system and the fundus camera optical system are about 1 mm and 4 mm respectively. In other words, the beam diameter of the fundus camera is larger than that of the OCT.

Here, a case is considered in which the anterior ocular segment to be imaged of the eye to be inspected has a partial haze caused by a cataract or the like near the ocular axis. At this time, when a tomographic image is acquired by aligning the optical axis of an illumination optical system with the ocular axis of the eye to be inspected, the irradiation light is blocked at the place in which the anterior ocular segment has a haze. Thus, a dark tomographic image is acquired. In light of this, the inspector may try to acquire a bright tomographic image by aligning the fundus with a non-blocked section of eye. This may be performed by observing the anterior ocular segment and shifting the optical axis of the illumination optical system away from the ocular axis.

As a result of this, however, there is a problem in that when a fundus image is acquired in a state in which the optical axis of the illumination optical system is shifted away from the ocular axis after the tomographic image is acquired, the irradiation light toward the anterior ocular segment causes vignetting or the like in the iris of the anterior ocular segment. In other words, while tomographic imaging may be successful even when the axes are not aligned, fundus imaging does require more careful aligning of the measurement beam with the fundus of the eye. Thus, generally, after a tomographic image is acquired, the inspector acquires a fundus image by aligning the optical axis of the illumination optical system with the ocular axis again.

However, if, after the tomographic image has been acquired by shifting the optical axis away from the ocular axis, the amount of shift of the optical axis from the ocular axis is small enough not to cause the vignetting in the fundus image after all, there may be no need to realign the optical axis of the illumination optical system with the ocular axis before the fundus image is acquired. Thus, the user of the apparatus (hereinafter, the inspector) may have wasted time in realigning the axes prior to beginning the fundus imaging. On the other hand, it may be very cumbersome for the inspector to determine whether or not alignment is required before the fundus imaging after the tomographic imaging, causing a reduction in diagnostic efficiency. It has thus been more efficient simply to realign the axes every time, prior to fundus imaging.

SUMMARY OF THE INVENTION

According to a first aspect of the invention, there is provided an ophthalmic apparatus comprising an irradiation unit that irradiates an eye to be inspected with a first beam for capturing a tomographic image of the eye and a second beam for capturing a fundus image of the eye, the acquisition of the fundus image being with a beam diameter larger than the beam diameter of the first beam. The apparatus further comprises a determination unit that, based on information indicating a shift amount between an irradiation position of the first beam in the eye to be inspected and an ocular axis of the eye to be inspected, determines whether or not the irradiation position falls within a range in which the fundus image can be captured, when the eye is irradiated with the second beam at the irradiation position.

The ophthalmic apparatus preferably can determine whether or not an irradiation position falls within a range in which a fundus image can be acquired (by visible light) based on a pre-imaging alignment step using infrared light. This alignment step gives rise to information (brightness, position, and the like of the fundus image acquired by the infrared light) that indicates an amount of shift from the irradiation position of a beam for the tomographic imaging, relative to an ocular axis of the eye being inspected. In this way, there can be provided an apparatus which can provide a tomographic image and a fundus image and which is easy for the inspector to use.

Further features of the present invention will become apparent from the following description of exemplary embodiments with reference to the attached drawings.

BRIEF DESCRIPTION OF THE DRAWINGS

FIGS. 1A and 1B show a method of controlling an optical image acquisition apparatus according to an embodiment of the present invention. FIG. 1A is a flowchart illustrating a method of controlling an optical image acquisition apparatus according to a first embodiment. FIG. 1B is a flowchart illustrating a method of controlling an optical image acquisition apparatus according to a second embodiment.

FIGS. 3A and 3B show an alignment screen according to the first and second embodiments of the present invention.

DESCRIPTION OF THE EMBODIMENTS

Preferred embodiments of the present invention will now be described in detail in accordance with the accompanying drawings.

First Embodiment

The first embodiment focuses on a configuration example of a method of controlling an optical image acquisition apparatus to which the present invention is applied.

The optical image acquisition apparatus of the present embodiment includes a tomographic imaging portion which captures a 3D tomographic image of a fundus of an eye using information based on an optical interference. The optical image acquisition apparatus also includes a fundus imaging portion which images a 2D fundus image using an observation pupil diameter larger than that of the tomographic imaging portion.

Figure 4A:
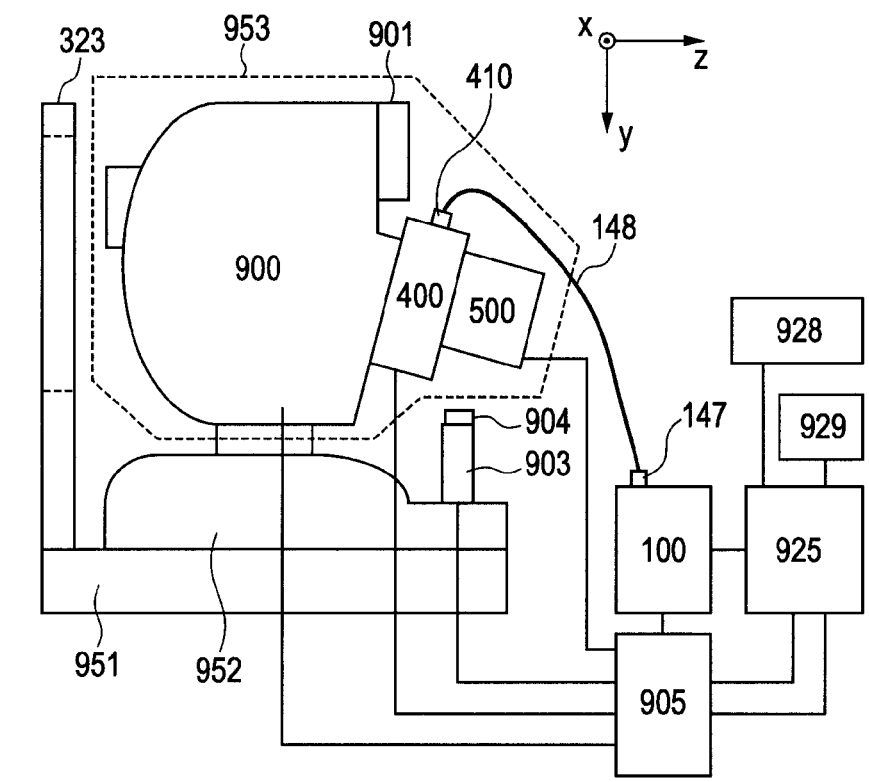
FIGS. 4A and 4B are schematic drawings showing an entire configuration of an ophthalmic apparatus according to the first and second embodiments of the present invention.
Figure 4B:
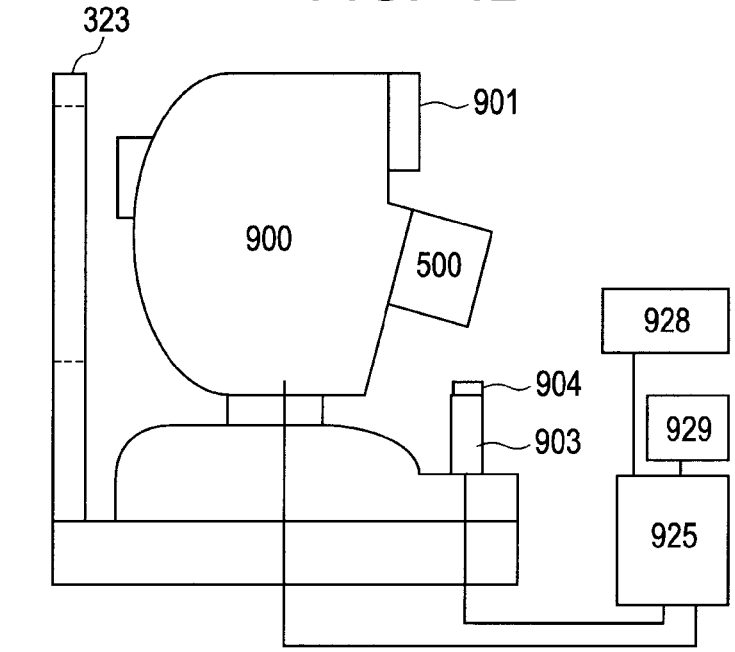

An example of an ophthalmic apparatus is illustrated in FIGS. 4A and 4B.

FIG. 4A is a side view of the ophthalmic apparatus 200, an interferometer portion 100, a fundus camera main body portion 900, an adapter 400, and a camera portion 500. Here, the fundus camera main body portion 900, the adapter 400, and the camera portion 500 are optically connected to each other.

The adapter 400 is movable relative to the fundus camera main body portion 900 (i.e. the adapter 400 and/or the fundus camera main body portion 900 are positionally adjustable to enable relative movement).

Thereby, coarse optical adjustment can be performed.

The adapter 400 and the interferometer portion 100 are optically connected to each other via an optical fiber 148. The adapter 400 and the interferometer portion 100 have a connector 410 and a connector 147 respectively. Therefore, the adapter 400 and the interferometer portion 100 are easy to attach and detach.

A control unit includes a personal computer 925 which performs configuration of the tomographic image and the like.

Further, the control unit includes a control circuit portion 905.

Further, the control unit includes a display monitor 928 and a storage portion 929 including a hard disk and the like. The control circuit portion 905 and the storage portion 929 may be disposed inside the personal computer 925.

The personal computer 925 and the control circuit portion 905 constitute the control unit according to the present embodiment. The ophthalmic apparatus 200 includes a chin rest 323 which fixes the chin and forehead of a patient so as to help fix the position of the eye of the patient that is to be inspected.

The ophthalmic apparatus includes a joystick 903 which constitutes an alignment portion for aligning the eye to be inspected and is operated by the inspector (i.e. the camera operator). The ophthalmic apparatus includes an operation button 904 for use in imaging operation input for tomographic imaging and fundus imaging.

The slide base portion 952 can be moved in an xz direction of FIG. 4A with respect to the fixed base portion 951 by operating the joystick 903.

The ophthalmic apparatus includes an unillustrated belt transmission mechanism and an unillustrated helicoid mechanism for vertically (i.e. in the y direction) moving an optical head portion 953 (enclosed by a dotted line in FIG. 4A). The optical head portion 953 includes an optical system related to imaging and is moved by rotating part of the joystick 903 for this movement in the y direction.

Thus, the operation of the joystick 903 allows an xyz alignment adjustment of the apparatus with respect to the eye to be inspected.

The ophthalmic apparatus includes a display unit 901 which displays image information and the like.

Alternatively, as illustrated in FIG. 4B, the fundus camera main body portion 900 and the camera portion 500 may constitute a fundus camera 700.

In this case, the interferometer portion 100 is not used, and thus the control circuit portion 905 does not need to be used. Further, the fundus camera 700 may be configured as the ophthalmic apparatus 200 by detaching the camera portion 500 from the fundus camera main body portion 900 and attaching the adapter 400 between the camera portion 500 and the fundus camera main body portion 900.

Figure 5A:
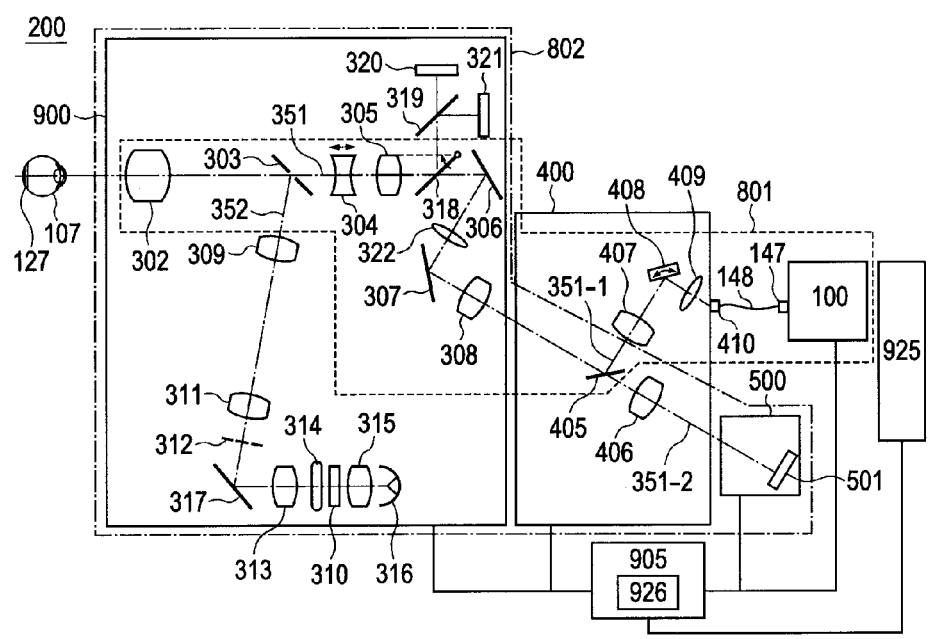
FIGS. 5A and 5B are schematic drawings showing a configuration of an optical system according to the first and second embodiments of the present invention.

Now, the configuration of the optical system of the ophthalmic apparatus including the adapter according to the present embodiment will be described using FIG. 5A.

First, the fundus camera main body portion 900 and the adapter 400 will be described. An object lens 302 is installed facing an eye to be inspected 107. An optical path on the optical axis is branched into an optical path 351 and an optical path 352 by a perforated mirror 303.

The optical path 352 constitutes an illumination optical system for illuminating the fundus of the eye to be inspected 107. The bottom portion of the fundus camera main body portion 900 includes a halogen lamp 316 for use in aligning the eye to be inspected 107 and a stroboscopic tube 314 for use in imaging the fundus of the eye to be inspected 107.

Here, the bottom portion of the fundus camera main body portion 900 also includes condenser lenses 313 and 315, and a mirror 317. The illumination light from the halogen lamp 316 and the stroboscopic tube 314 is converted to a ring-shaped light flux by a ring slit 312 which is reflected by the perforated mirror 303 to illuminate the fundus of the eye to be inspected 107.

The illumination light 352 will also be referred to as a second beam for acquiring a fundus image of the eye to be inspected, this second beam having a beam diameter (i.e. an outer diameter in the case of a ring-shaped beam) larger than the beam diameter of a first beam, which is for acquiring a tomographic image of the eye.

Further, the fundus camera main body portion 900 includes lenses 309 and 311, and an optical filter 310. In addition, the optical path 352 includes an unillustrated alignment optical system thereon. This is for projecting a split image: one portion intended for focusing on the fundus and a second portion intended to be a working dot which is an index for matching the eye to be inspected 107 with the optical axis of the optical system in the ophthalmic apparatus 200.

Alternatively, an alignment light source disposed outside the optical path 352 can also be used to project the working dot. For example, when two LEDs (light-emitting diodes) emitting infrared light as the alignment light source are disposed near the object lens and are lit, the working dot is formed near the anterior ocular segment of the eye to be inspected as a virtual image by cornea reflection of the eye.

The optical path 351 constitutes the optical system for imaging the tomographic image and the fundus image of the fundus of the eye to be inspected 107.

A focusing lens 304 and an imaging lens 305 are disposed on the right side (i.e. the sensor-side, rather than the eye-side) of the perforated mirror 303.

Here, the focusing lens 304 is supported such that when the inspector operates an unillustrated knob, the focusing lens 304 can be moved in a direction of the optical axis indicated by the double-headed arrow in the figure.

Next, the optical path 351 is guided to a fixation lamp 320 and an infrared area sensor 321 via a quick return mirror 318.

The quick return mirror 318 is configured to handle a wavelength range of infrared light for use in imaging the tomographic image such that light with a wavelength of about 800 nm or more is transmitted and light with a wavelength of about 800 nm or less is reflected.

The image information obtained by the infrared area sensor 321 is displayed on a display unit 901 or a monitor 928 (see FIGS. 4A and 4B) that can be used for aligning the eye for inspection.

Further, the fundus camera main body portion 900 includes a dichroic mirror 319 which is designed such that (of the light reflected from the quick return mirror 318) visible light is branched off in a direction of the fixation lamp 320 and infrared light is branched off in a direction of the infrared area sensor 321.

Next, the optical path 351 (i.e. the light transmitted through the quick return mirror 318) is guided to the adapter 400 side via a mirror 306, a field lens 322, a mirror 307, and a relay lens 308.

The adapter 400 is configured to include a dichroic mirror 405, relay lenses 406 and 407, a collimated lens 409, an XY scanner 408, and a connector 410.

In a case where the ophthalmic apparatus 200 is behaving as the fundus camera 700 illustrated in FIG. 4B, the relay lens 308 inside the fundus camera main body portion 900 is configured to form the fundus image on the area sensor 501 inside the camera portion 500 directly.

The optical path 351 is split off into an optical path 351-1 for tomographic imaging and an optical path 351-2 for fundus imaging using the dichroic mirror 405.

Note that the xy scanner 408 has been described as one mirror, but actually has two mirrors: an x scan mirror and a y scan mirror which are disposed close to each other. Further, the optical axis of the optical path 351-1 is adjusted to match the center of rotation of the two mirrors of the xy scanner 408.

The camera portion 500 is a digital single-lens reflex camera for imaging the fundus image. The adapter 400 is connected to the camera portion 500 via a general purpose camera mount. Therefore, it is easy to attach and detach.

The camera portion 500 includes an area sensor 501, on whose surface a fundus image is formed.

The ophthalmic apparatus 200 includes a control circuit portion 905, which further includes an image processing portion 926 as a determination portion which determines whether or not the fundus alignment state falls within an allowable range. The operation of the image processing portion 926 will be described later.

The ophthalmic apparatus 200 includes a tomographic imaging portion 801 (enclosed by a dotted line) and a fundus imaging portion 802 (enclosed by a dot-dashed line) according to the present embodiment.

The tomographic imaging portion 801 and the fundus imaging portion 802 share part of the optical system.

For example, the object lens 302, the perforated mirror 303, the focusing lens 304, the imaging lens 305, the quick return mirror 318, the mirror 306, the field lens 322, the mirror 307, the relay lens 308, the dichroic mirror 405 and the like, are shared.

Next, the configuration of the interferometer portion 100 will be described using FIG. 5B.

Figure 5B:
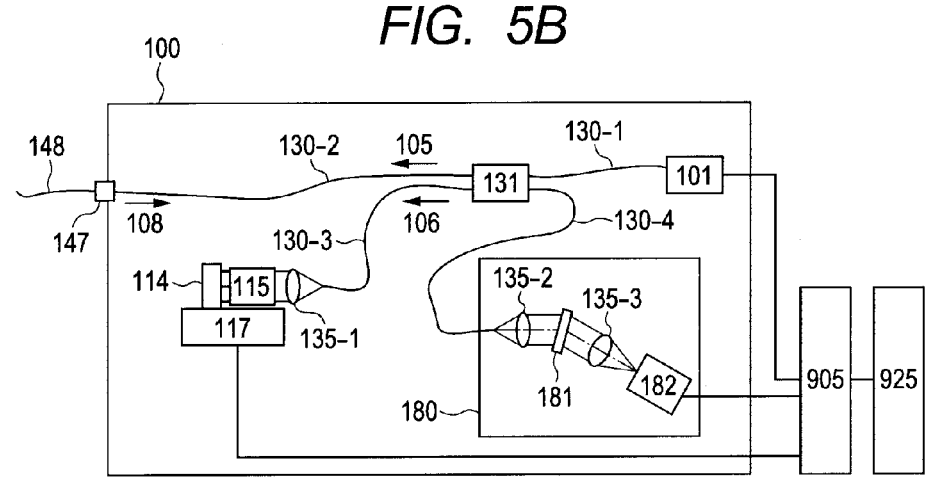

In FIG. 5B, the interferometer portion 100 includes a light source 101, a mirror 114, a dispersion compensation glass 115, an electrically driven stage 117, a control circuit portion 905, a single mode optical fiber 130 (made up of a plurality of optical fiber portions 130-1, etc., between devices), an optical coupler 131, a lens (or a plurality of lenses) 135, and a spectroscope 180. According to the present embodiment, the interferometer portion 100 acquires a tomographic image of a retina 127 (shown in FIG. 5A) of the eye to be inspected 107.

The interferometer portion 100 constitutes a Michelson interference system. The light (the first beam for acquiring the tomographic image of the eye to be inspected) emitted from the light source 101 is split into a measuring beam 105 and a reference beam 106 through an optical fiber 130-1 and the optical coupler 131.

The measuring beam 105 is connected to an optical fiber 148 through an optical fiber 130-2 and a connector 147. The measuring beam irradiated via the optical fiber 148 connected to the adapter 400 and the fundus camera main body portion 900 onto the retina 127 of the eye to be inspected 107 for observation is returned as a return beam 108 by reflecting or scattering on the retina 127, and the return beam reaches the optical coupler 131.

Meanwhile, the reference beam 106 reaches the mirror 114 through an optical fiber 130-3, a lens 135-1, and the dispersion compensation glass 115 inserted to compensate for dispersion of the measuring beam and the reference beam. The reference beam 106 is reflected from the mirror 114. Then, the reference beam 106 reaches the optical coupler 131 again by going back through the dispersion compensation glass 115, the lens 135-1, and the optical fiber 130-3.

The optical coupler 131 recombines the return beam 108 and the reference beam 106 into interference light.

Here, interference occurs when the optical path length of the measuring beam 105 and the return beam 108 (hereinafter referred to simply as the optical path length of the measuring beam 105) is substantially equal to the optical path length of the reference beam 106.

The mirror 114 is held on an electrically driven stage 117 which can be adjusted in a direction of the optical axis in such a manner that the optical path length of the reference beam 106 can be matched with the measuring beam 105, which is changing according to the eye being inspected 107.

The resultant interference light is guided to a spectroscope 180 through an optical fiber 130-4, in which the light is converted to parallel light through a lens 135-2, is split through a diffraction grating 181, and is formed into an image on a line sensor 182 through a lens 135-3.

Next, the light source 101 will be described.

The light source 101 is an SLD (Super Luminescent Diode) which is a typical low-coherence light source.

The central wavelength is 830 nm and the bandwidth is 50 nm. Here, the bandwidth is an important parameter because the bandwidth affects a resolution in a direction of the optical axis of the obtained tomographic image. The wavelength and bandwidth are thus chosen according to the ophthalmic apparatus characteristics.

In the present embodiment, an SLD is selected as the light source, but an ASE (Amplified Spontaneous Emission) or other light source may alternatively be used as long as low-coherence light can be emitted.

Considering that the central wavelength is used to measure the eye, near-infrared light is suitable. Further, the central wavelength is desirably as short a wavelength as possible since the central wavelength affects a lateral resolution of the obtained tomographic image. For the above two reasons, the central wavelength is set to 830 nm in the present embodiment.

The present embodiment uses a Michelson interferometer as the interferometer, but a Mach-Zehnder interferometer or other appropriate interferometer may be used.

It is desirable to use an appropriate interferometer according to the difference in the amount of light between the measuring beam and the reference beam such that when there is a large difference in the amount of light therebetween, a Mach-Zehnder interferometer may be used, and when there is a relatively small difference in the amount of light therebetween, a Michelson interferometer may be used.

Next, the image acquisition method for the tomographic image and the fundus image using the ophthalmic apparatus 200 will be described.

The ophthalmic apparatus 200 can generate the tomographic image of a desired position in the retina 127 by controlling the xy scanner 408.

The tomographic imaging is followed by the fundus imaging.

Here, the scan operation of the xy scanner 408 will be described using FIG. 2A.

First, the measuring beam 105 is projected in the −z direction and is scanned in the x direction in the figure, and the information of a predetermined number of images is acquired by the line sensor 182 from the imaging range in the x direction.

A linear image obtained at a position in the x direction is referred to as an A-scan image, and a 2D image of a plurality of A-scan images is referred to as a B-scan image.

After a plurality of A-scan images constituting a B-scan image are acquired, the scan position in the y direction is moved to scan in the x direction again, thereby obtaining a plurality of B-scan images in various positions in the y direction.

Next, the procedure for the method of controlling the optical image acquisition apparatus according to the present embodiment will be described using the flowchart illustrated in FIG. 1A.

Imaging processing starts in step 1001. An imaging program is executed by the personal computer 925 and an imaging screen is displayed on the monitor 928, and at the same time the xy scanner 408 is operated.

Then, in step 1002, a fundus alignment image is displayed. Specifically, after the measurement beam for the tomographic imaging has been aligned so as to create the best contrast (described below) and prior to the capture of the tomographic image or the fundus image, a fundus alignment image is created using infrared light from lamp 320. This image is received by a sensor 321 that will be described below and that is within the fundus camera main body 900 so that the sensors (500) used for the actual fundus imaging are not required at this stage. A tomographic alignment image is also created using light from lamp 316 to show the offset of the tomographic alignment axis with respect to the optical axis. The aligning process is contained within the fundus camera main body 900 so that other portions such as the adapter 400 and interferometer 100 need not be incorporated at this early stage. The display of the fundus alignment image will be described using FIGS. 3A and 3B.

Figure 3B:
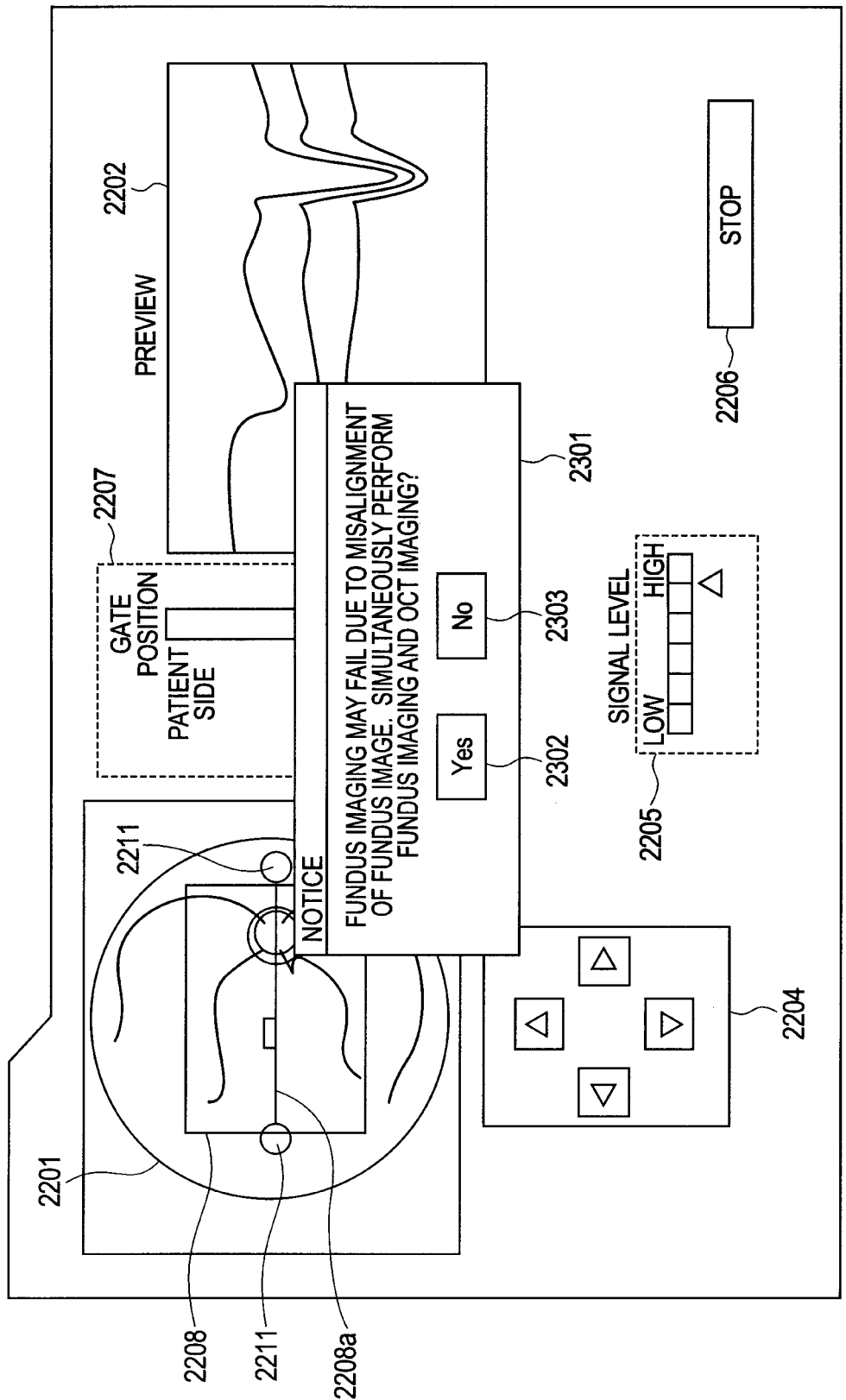

FIGS. 3A and 3B illustrate a fundus alignment image 2201 which is an infrared image obtained by the IR area sensor 321; a tomographic imaging alignment image 2202 for reference in alignment of the tomographic imaging; and a button 2204 for moving the scan range during tomographic imaging. The fundus imaging by infrared light may be performed not only by the IR area sensor 321 but also by the area sensor 501 if the later is available. More specifically, infrared light may be formed on the area sensor 501 by applying a medical camera without a filter blocking infrared light to the camera portion 500 which can be attached to and detached from the fundus camera main body portion 900 or the adapter 400. In this case, preferably, the dichroic mirror 405 is configured to transmit not only visible light for acquiring the fundus image but also infrared light and to reflect light for acquiring the tomographic image.

FIGS. 3A and 3B further illustrate an indicator 2205, a stop button 2206, and a slider 2207. In step 1002 of FIG. 1A, first, only the fundus alignment image 2201 is displayed.

The inspector aligns the ophthalmic apparatus 200 with the eye to be inspected 107. According to the specifications of the user interface in the present embodiment, while viewing the fundus alignment image 2201 or the display unit 901 displaying the same image, the inspector operates the joystick 903 for adjustment such that the working dot 2211 that the inspector can see in the fundus alignment image 2201 is located equally spaced in up, down, left, and right directions and is displayed at its finest resolution. The movement of the joystick by the inspector moves the alignment light relative to the eye being inspected. In this way, the working dots 2211 are generated and arranged such that they are in a predetermined position in the alignment image and on the eye relative to the light beam that will be used for the actual measurement. Thus, moving the working dots with respect to the fundus moves the camera and this moves the eventual position of the measurement beam.

Thus, the center of the optical axis of the apparatus can match the center of the optical axis of the eye to be inspected 107, and the distance between the eye to be inspected 107 and the object lens 302 can be appropriately set.

In addition, focusing of the camera relative to the fundus is adjusted using an unillustrated knob. At this time, the inspector makes an adjustment such that two splits 2212 match together horizontally in the alignment image. The alignment operation is the same as that for the conventional fundus camera and will be discussed no further herein.

Once the working dots 2211 and the splits 2212 are aligned as required, when the operation button 904 of the joystick is pressed once, the process moves to step 1003.

Regardless of step 1003, when the stop button 2206 is clicked on by an unillustrated mouse connected to the personal computer 925 (or indeed by a finger or stylus if the display is a touch-screen), the program terminates.

In step 1003, the light source 101 is activated to emit light such that a light flux for tomographic imaging is guided to the eye being inspected 107.

At the same time, the tomographic image alignment image 2202 of FIG. 3A is displayed. Note that the fundus alignment image 2201 continues to be displayed from the previous step.

The tomographic imaging alignment image 2202 is a tomographic image (B-scan) near a center line 2208a in a scan range 2208 illustrated in the fundus alignment image 2201.

For high-speed update display, the tomographic imaging alignment image 2202 is configured with fewer A scans than the number of A scans obtained by actual imaging.

The inspector adjusts the slider 2207 so as to display the tomographic image in the tomographic imaging alignment image 2202. Further, the inspector adjusts the gate position by operating the slider 2207 so as to brighten the tomographic image. This is in fact an adjustment for matching the optical path length of the reference beam 106 with the optical path length of the measuring beam 105. The slider operation involves movement of the position of mirror 114 by controlling the operation of the electrically driven stage 117 illustrated in FIG. 5B.

Hereinbefore, it has been described that the inspector adjusts the gate position, but automatic adjustment may be made based on luminance in the screen. The slider 2207 indicates the position in the inspector direction or in the patient direction in which the gate position is located, and serves as an adjustment guide.

The indicator 2205 indicates the ratio between a maximum luminance value of the displayed tomographic imaging alignment image 2202 and a luminance value of the background noise. The more rightward the indicator moves, the greater this ratio and the higher the image contrast is in the embodiment illustrated.

Here, a case in which the eye to be inspected 107 has a partial haze or opacity caused by a cataract, injury or the like will be described by referring to FIGS. 2A to 2C.

Figure 2A:
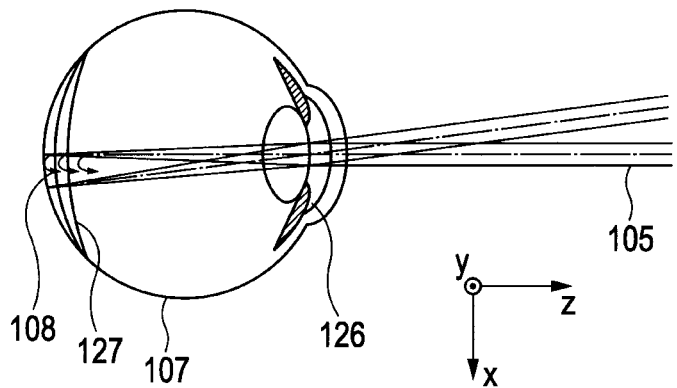
FIGS. 2A, 2B and 2C show an eye to be inspected and an observation light flux according to the first and second embodiments of the present invention.
Figure 2B:
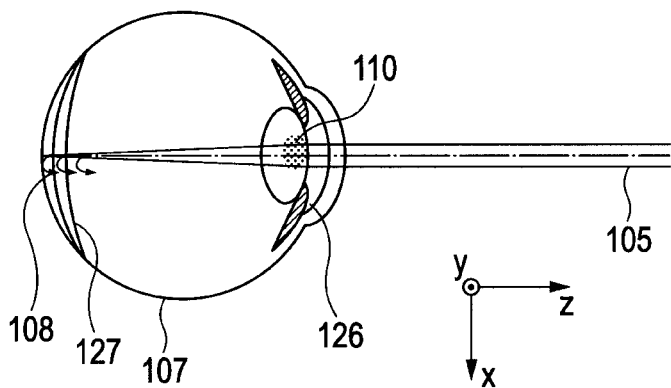
Figure 2C:
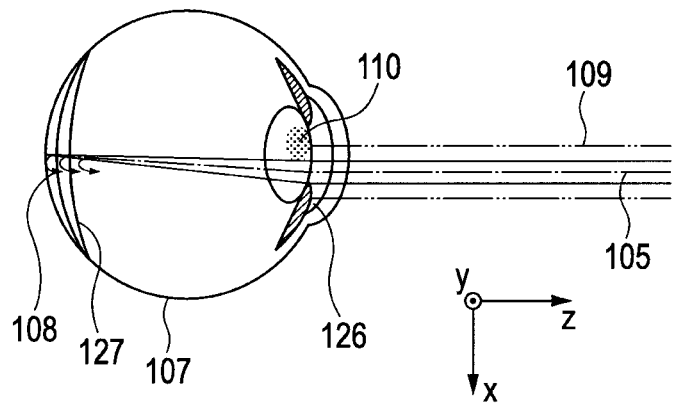

FIGS. 2A to 2C illustrate a light flux 105 of a measuring beam for tomographic imaging, an eye to be inspected 107, a light flux 109 for fundus imaging, a partial haze 110, an iris 126, and a fundus 127.

FIG. 2A illustrates a state in which a positional adjustment between a healthy eye to be inspected 107 and the optical head portion 953 is performed in step 1002.

In contrast to this, FIG. 2B illustrates a case in which the partial haze 110 is located for the most part in a center portion of the optical path. The light flux 105 of measuring beam for tomographic imaging is scattered by the partial haze and almost no light reaches the fundus 127.

Accordingly, the tomographic image in the tomographic imaging alignment image 2202 becomes very dark and does not take the desired A scan.

In this case, the inspector may adjust the measuring beam position so as to avoid the haze. To do this, the inspector makes an adjustment of the position of the optical head portion 953 using the joystick 903, particularly an adjustment in a direction perpendicular to the optical axis, and the light flux 105 of measuring beam for tomographic imaging can be guided to the fundus, avoiding the haze 110 (see FIG. 2C). Then, the tomographic image in the tomographic imaging alignment image 2202 becomes bright.

Meanwhile, as illustrated in FIG. 2C, the difference in observation pupil diameter (as opposed to eye pupil diameter) between the measurement beam for the fundus imaging (109) and the measurement beam for the tomographic imaging (105) causes the light flux 109 for fundus imaging to pass outside the light flux 105 for tomographic imaging. This is the case particularly for a light flux 109 that is ring-shaped, as mentioned above.

A result of the shifted tomographic imaging measurement beam 105 being surrounded by a larger diameter fundus imaging measurement beam 109 is that when the fundus is imaged in the state of FIG. 2C, the light flux for fundus imaging hits the iris 126 of the eye 107, rather than all entering through the pupil of the eye and causing a flare in part of the fundus image. This can be prevented using the following steps.

In step 1004, an alignment step is performed wherein infrared light is shone on the fundus along the path that the measurement beam for fundus imaging would take if the state in which the inspector has made an alignment adjustment in step 1003 has not been reversed or changed (in other words, the infrared light is shone around the path of the tomographic imaging measurement beam). The image processing portion 926 (also referred to as a determination unit; see FIG. 5A) determines whether or not the imaging position of the fundus imaging portion 802 (in the optical head portion 953) based on this alignment step is appropriate for fundus imaging.

Figure 6A:
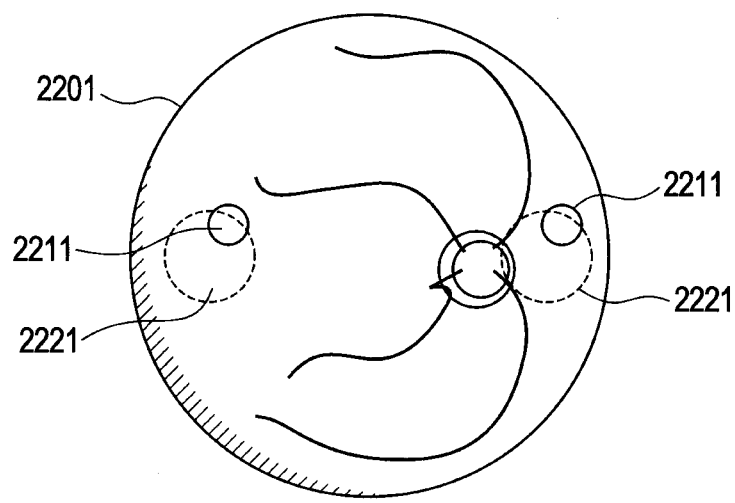
FIGS. 6A and 6B are schematic drawings showing a determination unit of a fundus alignment according to the first and second embodiments of the present invention.

The image processing portion 926 performs image processing on the fundus alignment image 2201. An example of the image processing will be described by referring to FIG. 6A. When the position of the working dot 2211 which is a high luminance point in the image is out of the setting range 2221, the imaging position of the fundus imaging portion 802 is determined to be out of the allowable range for the fundus image to be captured.

Figure 6B:
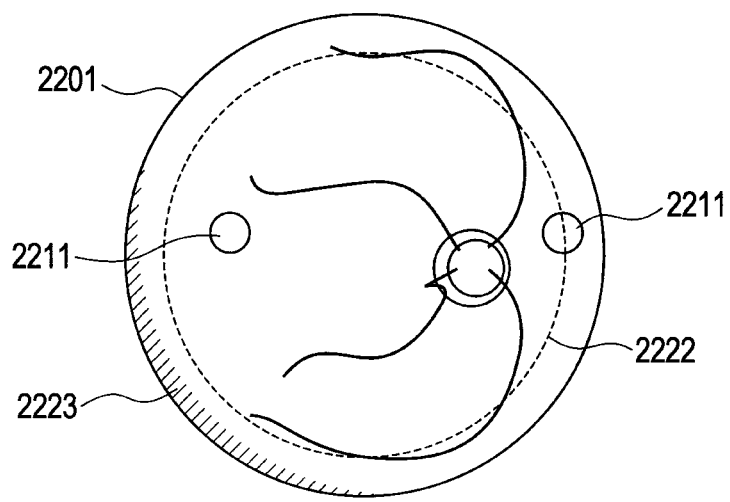

Another example of the image processing is described by referring to FIG. 6B. When the fundus alignment is shifted from the ocular axis, a portion 2223 corresponding to a bright peripheral portion of the fundus alignment image 2201 occurs. In light of this, an integrated value of the image luminance values of the peripheral area 2223 outside the border line 2222 is compared with an average value of the entire alignment image 2201. If the compared value is equal to or greater than a predetermined ratio, the imaging position of the fundus imaging portion 802 is determined to be out of the allowable range (i.e. a determination is made based on the brightness of the fundus imaged using infrared light).

In other words, the determination as to whether or not the irradiation position falls within the "fundus image acquirable range" is based on information (brightness, position, and the like of the above fundus image) indicating a "shift amount" between the optical axis of the illumination optical system and the ocular axis of the eye in the alignment stage before even the tomographic image is acquired. In determining the shift amount, first, the position of the working dot 2211 which is a high luminance point in the image is determined by means of image processing. Then, the distance between that position and the setting range 2221 is determined, which distance is the "shift amount." Since the position of the working dot corresponds to that of the optical axis, the positional shift of the working dot corresponds to that of the optical axis. Thus, there can be provided an apparatus which can provide a tomographic image and a fundus image, the apparatus being easy for the inspector to use.

A modification unit may be provided for reducing the beam diameter based on the shift amount when the fundus image is to be acquired. Alternatively, a movement unit may be provided for moving the optical axis of the illumination optical system closer to the ocular axis by an amount based on the shift amount when the fundus image is acquired. This eliminates vignetting in the iris of the anterior ocular segment when the fundus image is acquired. Thus, a bright fundus image can be acquired. Further, according to the above modification or the movement, it is preferable to use visible light to acquire the fundus image. Thus, the inspector can acquire a good fundus image free from cumbersome determination.

When a determination is made in step 1004 of FIG. 1A that the position of the fundus imaging portion falls within the allowable range, the process moves to step 1010 in which the process waits for pressing of the operation button 904. When the operation button 904 is pressed, the process moves to step 1011.

In step 1011, the tomographic imaging is performed. In this step, the quick return mirror 318 of the fundus camera main body portion 900 descends out of the way of the incoming beam 351 from the eye, and thus only the measuring beam 105 for tomographic imaging is guided to the dichroic mirror 405 portion for branching.

No light is guided at this stage to the camera portion 500 (as this is for the fundus imaging). Here, the XY scanner 408 is activated based on a preset scan specification. Then, the personal computer 925 reads an interfering signal in each fundus position from the line sensor 182 through the control circuit portion 905.

A beam with a split wavelength is incident on each pixel of the line sensor 182. Fourier transform is performed on intensity information of each wavelength obtained by the line sensor 182 and the obtained wavelength is the intensity information of the return beam 108 related to the depth direction in each fundus position.

This is a general principle of the SD (Spectral Domain)-OCT. The intensity information of the return beam 108 obtained by reading the line sensor 182 once is converted to image brightness. The linear image with that image brightness is the above described A-scan image. This is performed for each fundus position.

In step 1012, fundus imaging is performed automatically following step 1011 as follows.

When the predetermined tomographic image acquisition ends, the stroboscopic tube 314 is activated to emit light and at the same time, the quick return mirror 318 ascends back to a position intersecting with the measurement beam 351 to capture the fundus image using the camera portion 500. The fundus image is stored in the storage portion 929.

In step 1013, which follows automatically from step 1012, imaging ends.

On the other hand, when a determination is made in step 1004 that the position of the fundus imaging portion is out of the allowable range (i.e. the fundus imaging alignment is not appropriate), the process moves to step 1005, in which a message is displayed notifying the inspector that the fundus imaging might fail. Selection buttons are also displayed on the display screen and the process waits for a button selection.

As illustrated in FIG. 3B, a message indicating "Fundus imaging might fail due to misalignment of fundus image. Do you want to simultaneously perform fundus imaging and OCT imaging?" is displayed in a message box 2301.

Then, a button 2302 confirming the action (e.g. "YES") and a button 2303 cancelling the action (e.g. "NO") are displayed in the message box. The selection of one of the buttons 2302 and 2303 allows the selection of whether or not the imaging wait state is provided after tomographic imaging and before the fundus imaging.

When the button 2302 is selected in step 1006 by mouse click, the process moves to the above-described step 1010. The following operation is the same as described above.

When the button 2303 is selected in step 1006 by mouse click, the process moves to step 1007.

In step 1007, the process waits for pressing of the operation button 904 provided on the joystick 903. When the operation button 904 is pressed, the process moves to step 1008.

In step 1008, the tomographic imaging is performed. The operation of the tomographic imaging is the same as that in step 1011.

In step 1009, the process waits for pressing of the operation button 904 provided in the joystick 903.

Here, the inspector performs fundus alignment by referring to the fundus alignment image 2201 again. In this step, a message prompting the inspector for fundus alignment such as "Please make re-alignment for fundus imaging" may be displayed.

When the operation button 904 is pressed, the process moves to step 1012. The operation following step 1012 is the same as the above described operation.

Here, the state of displaying a prompt for re-alignment before the fundus imaging corresponds to the imaging wait state according to the present embodiment. Note that the display form is not limited to this, but any display may be used as needed. For example, the imaging wait state may be configured such that the fundus imaging is executed when the re-alignment is not executed within a predetermined time.

After the imaging ends, a 3D image and a fundus image made of an imaged B-scan image or a plurality of B-scan images are displayed on the monitor 928.

It has been described that step 1002 (fundus alignment image display) and step 1003 (tomographic imaging alignment image display) are performed in series, but both images may be simultaneously displayed or in the reverse order.

According to the present embodiment, the fundus imaging portion for imaging a 2D image of a fundus surface may be regarded as the fundus observation portion, and the same results may be obtained by a fundus observation unit with a larger observation pupil diameter (i.e. the diameter of the beam irradiated on an anterior ocular segment of the eye to be inspected) than the observation pupil diameter of the tomographic imaging portion.

Another example of the fundus observation portion is an autorefractometer which converts a refractive power to a numerical value from a reflected image of a light spot imaged on the fundus.

When the fundus camera is selected, a comparison can be made between the fundus image and the tomographic image which are closely related to each other, which is convenient for use in diagnosis.

Further, it has been described that the image processing portion 926 is included in the control circuit portion 905, but it may be included in the fundus camera main body portion 900 or the adapter 400, or it may be implemented as software running on the personal computer 925.

As described above, the ophthalmic apparatus according to the present embodiment can prevent fundus alignment from being shifted during fundus imaging.

Further, there is no need to perform any operations while simultaneously checking the tomographic imaging alignment image and the fundus alignment image, reducing cumbersome operation and burden of the inspector.

In the ophthalmic apparatus according to the present embodiment, the fundus camera portion comprises the fundus camera main body portion 900 and the camera portion 500, where the adapter 400 is detachably interposed between the fundus camera main body portion 900 and the camera portion 500.

Thus, the adapter 400 for splitting the optical path into the camera portion 500 and the interferometer portion 100 allows the apparatus to be used not only as a single fundus camera unit but also as an apparatus having a fundus imaging function, thereby improving use efficiency.

Second Embodiment

As the second embodiment, an ophthalmic apparatus having a configuration different from that of the first embodiment will be described.

The ophthalmic apparatus according to the present embodiment is different in configuration of the ophthalmic apparatus from that of the first embodiment in that an alignment is made under control of an actuator such as a motor.

Further, the present embodiment is different in image acquisition method from the first embodiment in that fundus re-alignment is automated.

The ophthalmic apparatus according to the present embodiment is configured such that an unillustrated sensor in the ophthalmic apparatus of FIG. 4A reads the operation of the joystick 903.

Based on the amount of operation, the control circuit portion 905 and the personal computer 925 control the unillustrated actuator to move the optical head portion 953 for alignment operation. According to the present embodiment, an actuator is provided in each xyz direction in the figure.

As the actuator, a general direct-acting actuator including a stepping motor and a rotation transmission mechanism having fine pitched screws and gears is used. Other actuator using different method may be used.

The configuration of each component of the optical system is the same as that of the first embodiment and thus the description thereof is omitted.

Next, the procedure for the method of controlling the optical image acquisition apparatus according to the present embodiment will be described using the flowchart illustrated in FIG. 1B.

Note that the description of a step of doing the same operation as a step of the first embodiment is omitted.

As illustrated in FIG. 1B, first, imaging starts in step 2001.

Then, in step 2002, an image for fundus alignment is displayed. In this step, the inspector aligns the ophthalmic apparatus 200 with the optical axis of the eye to be inspected 107. When the operation button 904 is pressed, the process moves to step 2003.

Then, in step 2003, the positional information of the optical head portion 953 is stored in the storage portion 929 of the personal computer 925.

The operation button 904 serves as the storage operation input portion only in the step 2003.

When the operation button 904 is pressed, the ophthalmic apparatus obtains a storage operation input signal.

According to the present embodiment, the positional information refers to the number of accumulated pulses indicating the amount of rotational movement of the stepping motor.

Then, the light source 101 is activated to emit light and the light flux 105 for tomographic imaging and measuring is guided to the eye to be inspected 107. Then, the process moves to step 2004.

Then, in step 2004, the tomographic image alignment image 2202 of FIGS. 3A and 3B are displayed.

The inspector adjusts the gate position and makes an alignment by the joystick to brighten the tomographic image in the tomographic imaging alignment image 2202. Then, the process automatically moves to step 2005.

Then, in step 2005, the image processing portion 926 determines whether or not the state adjusted by the inspector in step 2004 is appropriate for fundus imaging. This process is the same as that of the first embodiment.

Here, when a determination is made in step 2005 that the position of the fundus imaging portion falls within the allowable range, the process moves to step 2009.

In step 2009, the process waits for pressing of the operation button 904 provided in the joystick 903. When the operation button 904 is pressed, the process moves to step 2010.

In step 2010, the tomographic imaging is performed.

In step 2011 automatically moved from step 2010, the fundus imaging is performed. In step 2012 automatically moved from step 2011, imaging ends.

Meanwhile, when a determination is made in step 2005 that the position of the fundus imaging portion is out of the allowable range ("NO" in step 2005), the process moves to step 2006.

The process waits for pressing of the operation button 904 provided in the joystick 903. When the operation button 904 is pressed, the process moves to step 2007.

In step 2007, the tomographic imaging is performed (as described above). Then, the process automatically moves to step 2008. In step 2008, the optical head portion 953 is moved based on the positional information stored in step 2003.

Specifically, the stepping motor is rotated so as to match the stored number of accumulated pulses.

Then, the process automatically moves to step 2011. The following operation is the same as the above described operation.

As described above, the ophthalmic apparatus according to the present embodiment performs automatic return of the alignment position before fundus imaging depending on the fundus alignment state.

This can prevent fundus alignment from being shifted at fundus imaging.

Further, the inspector does not need to make a re-alignment at fundus imaging, thereby further reducing the burden of the inspector in comparison with the first embodiment.

Further, the method of controlling the optical image acquisition apparatus according to each embodiment described above may be implemented in such a manner that a program to be executed by a computer (e.g. a personal computer) corresponding to each controller implementing the control method is written and stored in a storage medium to be read by the computer.

Other Embodiments

Aspects of the present invention can also be realized by a computer of a system or apparatus (or devices such as a CPU—central processing unit or MPU—microprocessing unit) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-032330, filed Feb. 17, 2010, which is hereby incorporated by reference herein in its entirety.

What is claimed is:

1. An ophthalmic apparatus comprising:
   an irradiation unit configured to irradiate an eye to be inspected with a first light to capture a tomographic image of the eye to be inspected and with a second light to capture a fundus image of the eye to be inspected, the diameter of an irradiation area of the second light in the eye to be inspected being larger than the diameter of an irradiation area of the first light in the eye to be inspected; and
   a determination unit configured, based on information indicating a shift amount between an irradiation position of the first light in the eye to be inspected and an ocular axis of the eye to be inspected, to determine whether or not the irradiation position is within a range in which the fundus image can be captured.

2. The ophthalmic apparatus according to claim 1, further comprising a display control unit configured to control a display unit to display a warning when the determination unit determines that the irradiation position of the first light is out of the range.

3. The ophthalmic apparatus according to claim 2, wherein in response to the warning, a wait state occurs in the ophthalmic apparatus during which a selection by an operator is awaited of whether or not an irradiation position of the second light is to be changed.

4. The ophthalmic apparatus according to claim 1, further comprising a changing unit configured, when the determination unit determines that the irradiation position of the first light is out of the range, to change the diameter of the irradiation area of the second light in the eye to be inspected to a smaller diameter.

5. The ophthalmic apparatus according to claim 4, arranged to capture a fundus image of the eye to be inspected using the second light, the second light being visible light and being changed according to the changing of the changing unit.

6. The ophthalmic apparatus according to claim 1, further comprising a movement unit configured, when the determination unit determines that the irradiation position of the first light is out of the range, to move an irradiation position of the second light with respect to the eye to be inspected.

7. The ophthalmic apparatus according to claim 6, the apparatus being arranged to capture a fundus image of the eye being inspected using the second light, the second light being visible light and being positioned with respect to the eye being inspected according to the movement of the movement unit.

8. The ophthalmic apparatus according to claim 1, wherein the determination unit is configured to make the determination based on at least one of brightness of the fundus image of the eye to be inspected in the irradiation position of the first light and a distance between the fundus image and the ocular axis.

9. The ophthalmic apparatus according to claim 1, wherein the irradiation unit is configured to generate a fundus image of the eye to be inspected using infrared light, and
wherein the determination unit is configured to make a determination, based on the infrared fundus image, regarding whether the irradiation position of the second light will be within the range.

10. The ophthalmic apparatus according to claim 1, wherein the irradiation unit is configured to irradiate, when the irradiation position of the first light is within the range, the eye to be inspected with the second light.

11. An ophthalmic apparatus comprising:
an irradiation unit configured to irradiate an eye to be inspected with a first light to capture a tomographic image of the eye to be inspected and a second light to capture a fundus image of the eye to be inspected, the diameter of an irradiation area of the second light in the eye to be inspected being larger than the diameter of an irradiation area of the first light in the eye to be inspected; and
a movement unit configured to, when an irradiation position of the first light in the eye to be inspected is out of a range, move an irradiation position of the second light with respect to the eye to be inspected.

12. The ophthalmic apparatus according to claim 11, the apparatus being arranged to capture a fundus image of the eye to be inspected using the second first, the second first being visible light being positioned according to the movement of the movement unit.

13. An ophthalmic apparatus comprising:
an irradiation unit configured to irradiate an eye to be inspected with a first light to capture a tomographic image of the eye to be inspected and a second light to capture a fundus image of the eye to be inspected, the second light having a diameter of an irradiation area in the eye to be inspected larger than the diameter of an irradiation area of the first light in the eye to be inspected; and a changing unit configured, when an irradiation position of the first light in the eye to be inspected is out of a range, to change the diameter of the irradiation area of the second light in the eye to be inspected to a smaller diameter.

14. The ophthalmic apparatus according to claim 13, the apparatus being arranged to capture a fundus image of the eye to be inspected using the second light, the second light being visible light and being changed according to the changing of the changing unit.

15. An ophthalmic apparatus comprising:
an irradiation unit configured to irradiate an eye to be inspected with a first light to capture a tomographic image of the eye to be inspected and a second light to acquire a refractive power of the eye to be inspected, the second light having a diameter of an irradiation area in the eye to be inspected larger than the diameter of an irradiation area of the first light in the eye to be inspected; and
a determination unit configured, based on information indicating a shift amount between an irradiation position of the first light in the eye to be inspected and an ocular axis of the eye to be inspected, to determine whether or not the irradiation position is within a range in which the refractive power can be acquired.

16. The ophthalmic apparatus according to claim 15, wherein the irradiation unit is configured to irradiate, when the irradiation position of the first light is within the range, the eye to be inspected with the second light.

17. An ophthalmic method comprising:
irradiating an eye to be inspected with a first light to capture a tomographic image of the eye to be inspected;
determining, based on information indicating a shift amount between an irradiation position of the first light in the eye to be inspected and an ocular axis of the eye to be inspected, whether or not the irradiation position is within a range in which a fundus image of the eye to be inspected can be captured; and
irradiating, when the irradiation position of the first light is within the range, the eye to be inspected with a second light to capture the fundus image,
wherein the diameter of an irradiation area of the second light in the eye to be inspected is larger than the diameter of an irradiation area of the first light in the eye to be inspected.

18. A non-transitory computer-readable storage medium for storing a computer program that causes a computer to execute the ophthalmic method according to claim 17.

19. The ophthalmic method according to claim 17, further comprising controlling a display unit to display a warning when the determining step determines that the irradiation position of the first light is out of the range.

20. The ophthalmic method according to claim 17, wherein in response to the warning, a wait state occurs during which a selection by an operator is awaited of whether or not an irradiation position of the second light is to be changed.

21. The ophthalmic method according to claim 17, further comprising changing, when the irradiation position of the first light is out of the range, the diameter of the irradiation of the second light in the eye to be inspected to a smaller diameter.

22. The ophthalmic method according to claim 21, further comprising capturing a fundus image of the eye to be inspected using the second light, the second light being visible light and being changed according to the changing.

23. The ophthalmic method according to claim 17, further comprising moving, when the irradiation position of the first light is out of the range, an irradiation position of the second light with respect to the eye to be inspected.

24. The ophthalmic method according to claim 23, further comprising capturing a fundus image of the eye being inspected using the second light, the second light being visible light and being positioned with respect to the eye being inspected according to the moving.

25. The ophthalmic method according to claim 17, wherein determining, in the determining step, is based on at least one of brightness of the fundus image of the eye to be inspected in the irradiation position of the first light and a distance between the fundus image and the ocular axis.

26. The ophthalmic method according to claim 17, further comprising generating a fundus image of the eye to be inspected using infrared light,
wherein determining, in the determining step, is based on the infrared fundus image, regarding whether the irradiation position of the second light will be within the range.

27. An ophthalmic method comprising:
irradiating an eye to be inspected with a first light to capture a tomographic image of the eye to be inspected; and
moving, when an irradiation position of the first light in the eye to be inspected is out of a range, an irradiation position of the second light with respect to the eye to be inspected; and
irradiating, after the moving, the eye to be inspected with a second light to capture a fundus image of the eye to be inspected, the diameter of an irradiation area of the second light in the eye to be inspected being larger than the diameter if ab urraduatuib area of the first light in the eye to be inspected.

28. The ophthalmic method according to claim 27, further comprising capturing a fundus image of the eye to be inspected using the second light, the second light being visible light and being positioned according to the moving.

29. A non-transitory computer-readable storage medium for storing a computer program that causes a computer to execute the ophthalmic method according to claim 27.

30. An ophthalmic method comprising:
irradiating an eye to be inspected with a first light to capture a tomographic image of the eye to be inspected;
changing, when an irradiation position of the first light in the eye to be inspected is out of a range, the diameter of a second light to capture a fundus image of the eye to be inspected to be a smaller diameter, the second beam having a diameter of an irradiation area in the eye to be inspected larger than the diameter of an irradiation area of the first light in the eye to be inspected; and
irradiating, after the changing, an eye to be inspected with the second light having the changed diameter.

31. The ophthalmic method according to claim 30, further comprising capturing a fundus image of the eye to be inspected using the second light, the second light being visible light and being changed according to the changing.

32. A non-transitory computer-readable storage medium for storing a computer program that causes a computer to execute the ophthalmic method according to claim 30.

33. An ophthalmic method comprising:
irradiating an eye to be inspected with a first light to capture a tomographic image of the eye to be inspected;
determining, based on information indicating a shift amount between an irradiation position of the first light in the eye to be inspected and an ocular axis of the eye to be inspected, whether or not the irradiation position is within a range in which a refractive power of the eye to be inspected can be acquired; and
irradiating, when the irradiation position of the first light is within the range, an eye to be inspected with a second light to acquire the refractive power,
wherein the diameter of an irradiation area of the second light in the eye to be inspected is larger than the diameter of an irradiation area of the first light in the eye to be inspected.

34. A non-transitory computer-readable storage medium for storing a computer program that causes a computer to execute the ophthalmic method according to claim 33.

* * * * *